(12) United States Patent
Wimer et al.

(10) Patent No.: US 8,240,202 B2
(45) Date of Patent: Aug. 14, 2012

(54) HAND DYNAMOMETER WITH IMPROVED CONFIGURATION FOR GRIP STRENGTH ASSESSMENT

(75) Inventors: Bryan Wimer, Morgantown, WV (US); Daniel E. Welcome, Morgantown, WV (US); Christopher Warren, Belle Vernon, PA (US); Thomas W. McDowell, Fairmont, WV (US); Ren G. Dong, Morgantown, WV (US)

(73) Assignee: Centers for Disease Control and Prevention, Altanta, GA (US)

( * ) Notice: Subject to any disclaimer, the term of this patent is extended or adjusted under 35 U.S.C. 154(b) by 284 days.

(21) Appl. No.: 12/773,420

(22) Filed: May 4, 2010

(65) Prior Publication Data

US 2010/0281974 A1 Nov. 11, 2010

Related U.S. Application Data

(60) Provisional application No. 61/175,473, filed on May 5, 2009.

(51) Int. Cl.
*A63B 21/02* (2006.01)
(52) U.S. Cl. .................................. 73/379.03
(58) Field of Classification Search ............... 73/379.03, 73/397.02, 862.245, 862.541, 800
See application file for complete search history.

(56) References Cited

U.S. PATENT DOCUMENTS

| 5,467,656 | A | * | 11/1995 | Teare et al. | ............ 73/862.541 |
| 7,467,551 | B1 | * | 12/2008 | Yang | .......................... 73/379.03 |
| 2009/0192522 | A1 | * | 7/2009 | Blumenkranz | ............... 606/130 |

OTHER PUBLICATIONS

Dong R.G., Wu J.Z., Welcome D.E., McDowell T.W., "A New Approach to Characterize Grip Force Applied to a Cylindrical Handle", Medical Engineering and Physics 30 (2008): 20-33.
Nicol, A.C., Chadwick, E.K.J., "A Novel Force Transducer for the Measurement of Grip Force", Journal of Biomechanics 34 (2001), 125-128.
Pronk, C.N.A., and Niesing, R., "Measuring Hand-Grip Force Using a New Application of Strain Gauges", Medical and Biological Engineering & Computing 19 (1981), 127-128.

* cited by examiner

*Primary Examiner* — Jewel V Thompson
(74) *Attorney, Agent, or Firm* — Gifford, Krass, Sprinkle, Anderson & Citkowski, P.C.

(57) ABSTRACT

A handle assembly mounted to a dynamometer measuring device including a base mounted to an input location of the measuring device. A plurality of arms extend in a lineal direction from the base and are arranged in spaced and gap defining fashion. The arms deflect inward relative to one another upon being exerted by a compressing force and concurrent with outputting a signal through at least one strain gauge wire extending from an interior of each arm to the measuring device.

16 Claims, 3 Drawing Sheets

HAND DYNAMOMETER WITH IMPROVED CONFIGURATION FOR GRIP STRENGTH ASSESSMENT

CROSS-REFERENCE TO RELATED APPLICATIONS

This Application claims the benefit of U.S. Provisional Application 61/175,473 filed on May 5, 2009.

STATEMENT REGARDING FEDERALLY SPONSORED RESEARCH OR DEVELOPMENT

The invention described herein may be manufactured, used, and licensed by or for the United Stated Government.

FIELD OF THE INVENTION

The present invention relates generally to grip strength measurement devices. More specifically, the present invention discloses a cylindrically or modified triangular configured hand dynamometer such as is applied to the medical community for use in measuring grip strength in patients suffering from a wide range of conditions such as hand-arm vibration syndrome, carpel tunnel syndrome, other disorders of the upper extremities or those recovering from health issues like stroke. Among numerous additional potential applications, such hand dynamometers have also been employed in a therapeutic capacity as an exercise tool for the elderly to help strengthen grip and reduce blood pressure.

BACKGROUND OF THE INVENTION

Grip strength (also defined as force) measurement is a measure of the grip capability of the human hand. The purpose of a dynamometer (handle meter) is to assist in measuring an individual's grip strength. This can be of assistance in the diagnosis of musculoskeletal disorders of the hand as well as to monitor the recovery progress following hand surgery or injury. Problems associated with prior art designs for dynamometers for hand strength testing include such as pain during gripping (which could affect the test results for someone with an injury) and the potential for results that could not be accurately repeated.

SUMMARY OF THE INVENTION

The present invention discloses a handle assembly mounted to a dynamometer measuring device including a base mounted to an input location of the measuring device. Arms are provided and extend in a generally lineal direction from the base. The arms are arranged in a predetermined spaced and gap defining fashion. The arms deflect inward relative to one another, upon being exerted by a compressing force and concurrent with outputting a signal through at least one strain gauge wire extending from an interior of each arm to the measuring device.

Additional features include each of the arms exhibiting a modified triangular shape with a slightly convex outer surface and inwardly angled sides which define an acute angle such that, upon assembly of the arms in a generally pie cross sectional shape, the arms collectively define a rounded circular outer profile and a three dimensional elongated cylindrical shape. A pair of strain gauges are included per individual arm, these being seated within recessed defined pockets within the arms and at a location proximate the base. An extending channel is defined within the base through which the strain gauge wires pass to attach to a data acquisition system associated with the dynamometer measuring device.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As previously described, the present invention discloses an improved and generally cylindrical overall shaped dynamometer constructed from a plurality of individual and modified triangular handle meters which is designed to measure an individuals grip strength. As previously described, the hand dynamometer is useful in helping to diagnose the musculoskeletal disorders of the hand and to monitor the recover progress after a hand surgery or injury.

Referring again to FIG. 1, a cylindrical shaped dynamometer is generally shown at 10 and includes a base (see as generally shown at 12), such as which is fastened or connected to an appropriate device or assembly (not shown) for receiving and subsequently modifying a signal representative of a generated input force. Additionally not shown but understood to exist is the provision of appropriate mechanical to electrical signal technology for sensing the exertion of a mechanical force, converting the same to a digital or other electronic related scale, and transmitting a signal representative of the reading to an appropriate output.

Figure 2:
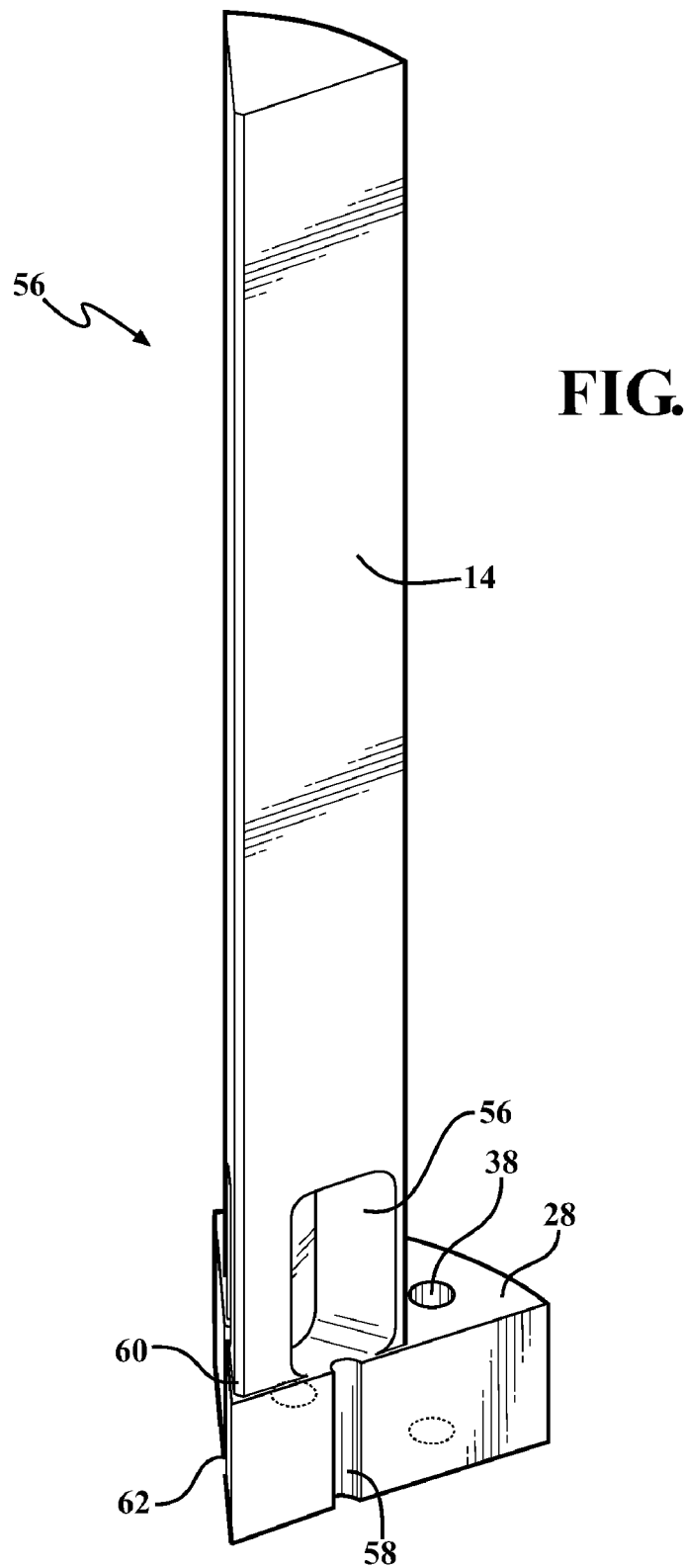
FIG. 2 is an illustration of a selected and modified triangular shaped portion associated with the dynamometer handle according to the present inventions.
Figure 3:
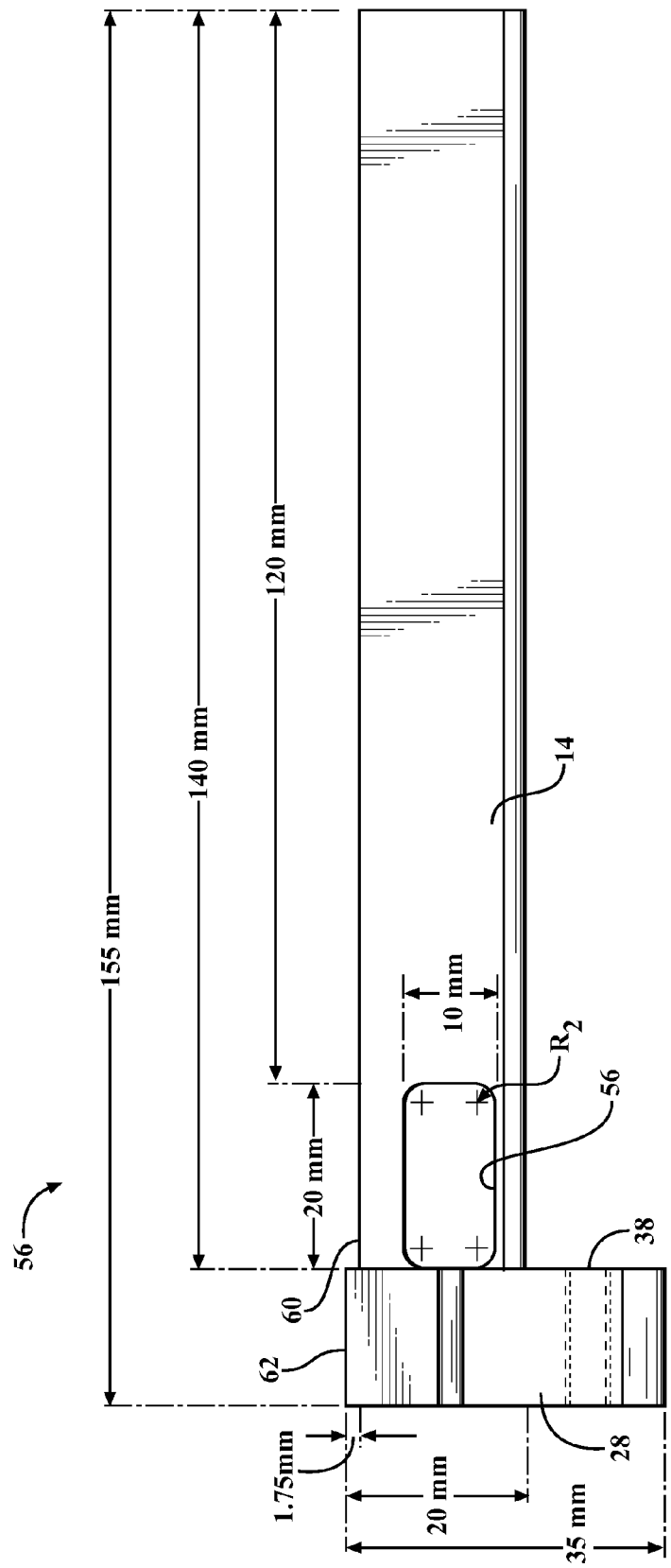
FIG. 3 is a side diagrammatic view illustration of the variant of FIG. 2.

The dynamometer further exhibits a plurality of six individual elongate portions, (also termed arms) and which are shown at 14, 16, 18, 20, 22 and 24. As is shown in FIGS. 2 and 3, the configuration of each of the individual elongate portions 14-24 (further represented in FIG. 2 as selected portion 14) is such that they each exhibit a modified triangular shape with a slightly convex (or outwardly projecting) side, such that the elongate portions collectively define a generally cylindrical shape. As shown, the outer surface associated with each arm exhibits an angle of 60°, with the six in total establishing the 360° circumferential rounded outer profile and a corresponding three dimensional elongated cylindrical shape. That said, it is also envisioned and understood that any plurality of individual arms or elongate portions, ranging from two, three, four, five, seven or more can be incorporated into alternate variants and within the scope of the invention.

The base 12 exhibits a generally circular profile and in a preferred embodiment represents a common assembled base. Without limitation, this can be further defined by the side-by-side aligning arrangement of outwardly annular projecting ends 26, 28, 30, 32, 34 and 36 corresponding to the elongate portions 14, 16, 18, 20, 22 and 24. As further shown, a plurality of apertures 38 extend in a linear direction through the annular projecting ends, around its collective circumference, and so that a plurality of mounting fasteners (not shown) can be used to mount the dynamometer assembly to a desired input location such as corresponding to a housing associated with the testing device.

Figure 1:
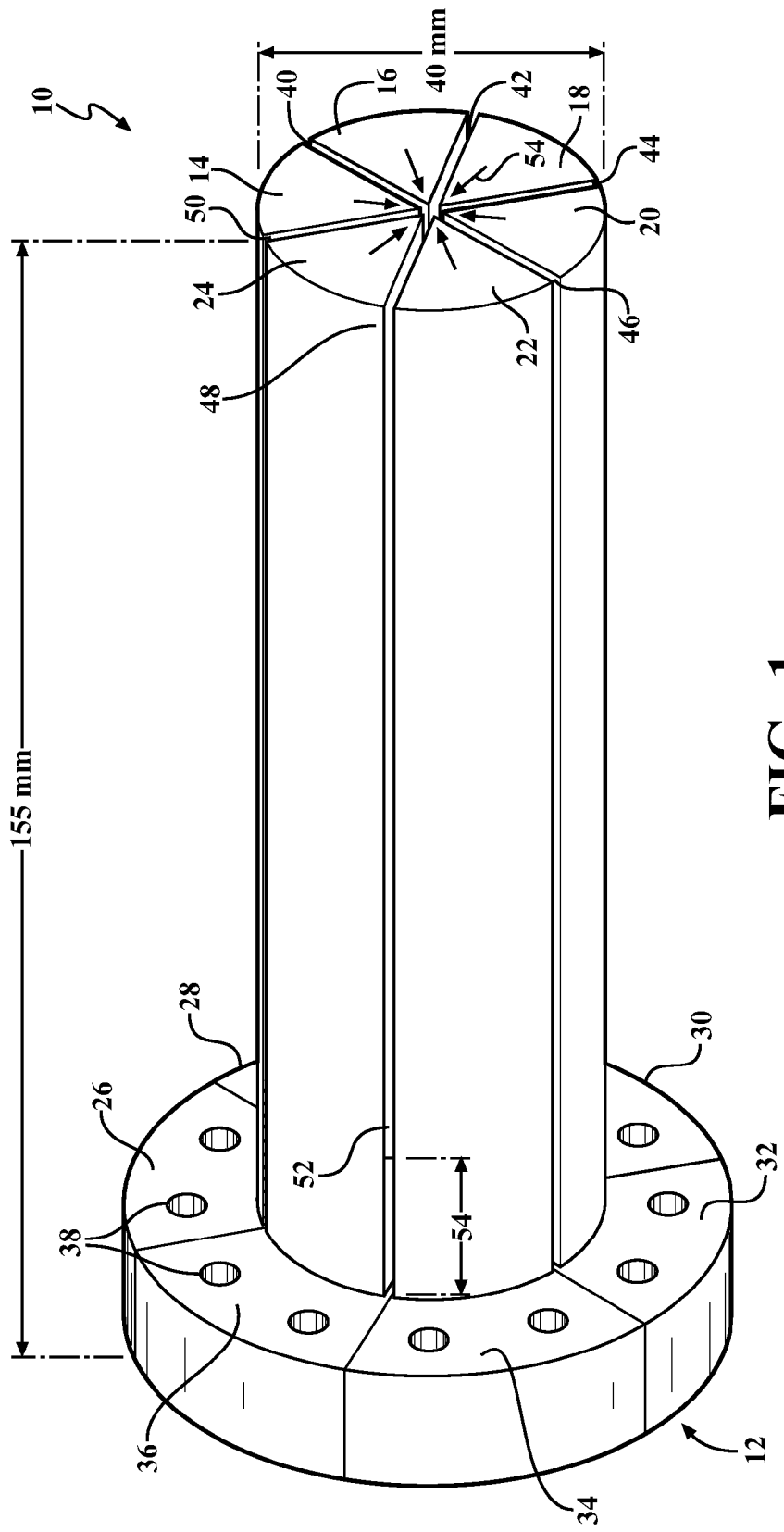
FIG. 1 is a perspective view of the dynamometer according to one preferred embodiment and which the cylindrical handle is illustrated as a plurality of six individual elongate portions terminating in a mounting base and exhibiting a desired gap or spacing therebetween for permitting inward and force measuring deflection of the elongate portions.

As further shown in FIG. 1, a gap or spacing (see at 40, 42, 44, 46, 48 and 50) is defined in linear extending fashion along a boundary associated with each mating pair of modified triangular elongate and gripping portions, e.g. as illustrated by boundary gap 40 between portions 14 and 16, gap 42 between portions 16 and 18, gap 44 between portions 18 and 20, gap 46 between portions 22 and 20, gap 48 between portions 24 and 22 and, finally, gap 50 between portions 24 and 14. As further shown, the linear extending gaps terminate at locations a predetermined distance (see for example at 52 associated with gap 48) short of the boundary location defined with the annular projecting base portions (see also corresponding indicated distance 54 between the inner end of the gap 48 and the annular projecting end). The degree of spacing or gapping, is determined according to the material properties of the elongate arm portions, as well as the desired testing parameters of the dynamometer assembly however, and as illustrated, can vary from some fraction less than 1 mm up to several mm.

In this fashion, the generally circular outer profile exhibited by the assembled and gap spaced elongated and modified triangular shaped portions 14-24 is capable of being more ergonomically and comfortably grasped by a user. Further, and upon being compressed, the dynamometer handle design more accurately records and converts a readout signal associated with the handle. The data collection occurs by virtue of the collective inward (compressing) deflection of the individual of the handle portions (see arrows 54), the inner tapered edges of each of the arms deflecting towards one another in the fashion shown.

The interior architecture associated with the handle design 10 includes an accessible recessed and lowermost location 56, this defined within the handle 14 as shown in FIG. 2. Strain gauge wires (not shown) extend from the recessed location 56 through an aperture 58 defined in the assembled base portion 28 and into the associated design machine. In this fashion, the assembled triangular shaped portions operate to convert a degree of mechanical compressive force applied to a signal which is transmitted via the inner extending wires (again not shown in FIG. 2) to the assembly housing upon which the dynamometer handle assembly 10 is mounted.

The configuration and dimension of the assembled elongate triangular portions, such as in one non-limiting and preferred embodiment, defines a handle configuration of 40 mm diameter and 155 mm length. Referring further to the side view of FIG. 3, additional dimensions associated with the illustrated embodiment include the dedicated height of the elongated portions (as measured from a top edge of the annular projecting base) being 140 mm, a further reduced 120 mm extending from a top surface of the recessed profile 56, the profile further exhibiting a height of 20 mm and a width of 10 mm. Finally, the annular projecting end portions exhibit a maximum outer radial (cross sectional) dimension of 35 mm, the associated triangular shaped portion exhibiting a maximum cross sectional dimension of 20 mm, and a fairly minute gap of 1.75 mm exhibited between a mating inner tapered edge of the triangular shaped portion (see at 60 in FIG. 2) and a corresponding inner tapered edge (further at 62) associated with the projecting base portion. It is also envisioned and understood that material constructions associated with the handle design can include any of aluminum and titanium, metal composite or other materials exhibiting the desired properties of elongated spring deformation (also known as cantilever deformation) and resilience.

Additional to the disclosure presented above, other arrangements can be made in which different handle diameters and lengths are used. The handle is further unique in the fact that it uses shear strain gauges to measure the force applied to the arm. By measuring the shear strain the force level recorded on the handle will be independent of load location.

In one preferred application, there further exist two gauges per individual triangular shaped arm portion, and which are placed within the recessed defined areas (or pockets as again shown at 56 in FIG. 2 located near the base of the handle. The extending channel 58 is again provided for the strain gauge wires to pass through the base of the handle, allowing them to attach to the data acquisition system previously described and associated with a housing to which the handle assembly 10 is mounted.

The cylindrical handle meter can provide more useful information and more reliable grip strength measurement for the following reasons: 1. the cylindrical shape of the handle is more comparable with the tool and mechanical handles widely used at workplaces, 2. it is more comfortable for a person to grip on the cylindrical handle than other prior art handle designs, 3. the measured strength on the cylindrical handle represents the total grip force that can be used for tool and machine ergonomic design, together with the friction force and torque that can also be estimated from the total grip force, 4. the grip force distributed at the different parts of the hand can be measured on the cylindrical handle meter which may be important information for the diagnosis of hand disorders."

Additionally, and whereas the basic functions associated with the handle dynamometer exhibit similarities previously known dynamometer handles that are currently used for such grip strength measurement, the provision of the cylindrical handle meter constitutes an improvement over prior art handle designs in that it provides more useful information and more reliable grip strength measurement for the following reasons: (I) the cylindrical shape of the handle is more comparable with the tool and machine handles widely used at workplaces; (II) it is more comfortable for a person to grip on the cylindrical handle than is associated with other prior art handle designs; (III) the measured strength on the cylindrical handle represents the total grip force that can be directly used for tool and machine ergonomic designs, together with the friction force and torque that can also be estimated from the total grip force; (IV) the grip force distributed at the different parts of the hand can be measured on the cylindrical handle meter, which may be important information for the diagnosis of the hand disorders.

It is further envisioned that the cylindrical and triangular shaped handle meter present a wide range of applications. For example, these can be used to help diagnosis hand-arm vibration syndrome, carpel tunnel syndrome, and other disorders of the upper extremities. It can be used as one of approaches to examine the hand strength for job requirement, to monitor the recover progress after a hand surgery or injury, and to collect grip strength data for tool and machine design.

Having described our invention, other and additional preferred embodiments will become apparent to those skilled in the art to which it pertains, and without deviating from the scope of the appended claims.

We claim:

1. A handle assembly for use with a dynamometer measuring device, said assembly comprising:

a base adapted for mounting to an input location of the measuring device;

a plurality of arms extending linearly from said base, said arms being arranged in spaced and gap defining fashion; and upon application of a compressing force, said arms deflecting inwardly relative to one another and outputting a signal through at least one strain gauge wire extending from an interior of each arm to the measuring device.

2. The assembly as described in claim 1, each of said arms exhibiting a modified triangular shape with a slightly convex outer surface, such that said arms collectively define a rounded circular outer profile and a three dimensional elongated cylindrical shape.

3. The assembly as described in claim 1, further comprising a pair of strain gauges per individual arm and which are seated within recessed defined pockets within said arms and at a location proximate said base.

4. The assembly as described in claim 3, further comprising an extending channel defined within said base through which the strain gauge wires pass to attach to a data acquisition system associated with the dynamometer measuring device.

5. The assembly as described in claim 2, further comprising a plurality of six arms.

6. The assembly as described in claim 5, each of said arms further comprising an annular projecting end, a plurality of apertures extending through each of said projecting ends, around its collective circumference for receiving mounting fasteners to mount said assembly to the measuring device.

7. A handle assembly for use with a dynamometer measuring device, said assembly comprising:

a base adapted for mounting to an input location of the measuring device;

a plurality of arms extending linearly from said base, said arms being arranged in spaced and gap defining fashion, each of said arms exhibiting a modified triangular shape with a slightly convex outer surface, such that said arms collectively define a rounded circular outer profile and a three dimensional elongated cylindrical shape; and upon application of a compressing force, said arms deflecting inwardly relative to one another and outputting a signal through at least one strain gauge wire extending from an interior of each arm to the measuring device.

8. The assembly as described in claim 7, further comprising a pair of strain gauges per individual arm and which are seated within recessed defined pockets within said arms and at a location proximate said base.

9. The assembly as described in claim 8, further comprising an extending channel defined within said base through which the strain gauge wires pass to attach to a data acquisition system associated with the dynamometer measuring device.

10. The assembly as described in claim 7, further comprising a plurality of six arms.

11. The assembly as described in claim 10, each of said arms further comprising an annular projecting end, a plurality of apertures extending through each of said projecting ends, around its collective circumference for receiving mounting fasteners to mount said assembly to the measuring device.

12. A handle assembly for use with a dynamometer measuring device, said assembly comprising:

a base adapted for mounting to an input location of the measuring device;

a plurality of arms extending linearly from said base, said arms being arranged in spaced and gap defining fashion, a pair of strain gauges per individual arm and which are seated within recessed defined pockets within said arms and at a location proximate said base; and upon application of a compressing force, said arms deflecting inwardly relative to one another and outputting a signal through at least one strain gauge wire extending from an interior of each arm to the measuring device.

13. The assembly as described in claim 12, each of said arms exhibiting a modified triangular shape with a slightly convex outer surface, such that said arms collectively define a rounded circular outer profile and a three dimensional elongated cylindrical shape.

14. The assembly as described in claim 12, further comprising an extending channel defined within said base through which the strain gauge wires pass to attach to a data acquisition system associated with the dynamometer measuring device.

15. The assembly as described in claim 13, further comprising a plurality of six arms.

16. The assembly as described in claim 15, each of said arms further comprising an annular projecting end, a plurality of apertures extending through each of said projecting ends, around its collective circumference for receiving mounting fasteners to mount said assembly to the measuring device.

* * * * *

UNITED STATES PATENT AND TRADEMARK OFFICE
CERTIFICATE OF CORRECTION

PATENT NO. : 8,240,202 B2
APPLICATION NO. : 12/773420
DATED : August 14, 2012
INVENTOR(S) : Bryan Wimer et al.

It is certified that error appears in the above-identified patent and that said Letters Patent is hereby corrected as shown below:

Col. 1, line 15: replace "United Stated" with --United States--

Signed and Sealed this
Second Day of April, 2013

Teresa Stanek Rea
*Acting Director of the United States Patent and Trademark Office*